US012629018B2

(12) United States Patent
Vakoc et al.

(10) Patent No.: US 12,629,018 B2
(45) Date of Patent: May 19, 2026

(54) USING THE DYNAMIC FORWARD SCATTERING SIGNAL FOR OPTICAL COHERENCE TOMOGRAPHY BASED FLOW QUANTIFICATION

(71) Applicant: The General Hospital Corporation, Boston, MA (US)

(72) Inventors: Benjamin J. Vakoc, Arlington, MA (US); Ahhyun Stephanie Nam, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 309 days.

(21) Appl. No.: 18/681,962

(22) PCT Filed: Aug. 8, 2022

(86) PCT No.: PCT/US2022/074653
§ 371 (c)(1),
(2) Date: Feb. 7, 2024

(87) PCT Pub. No.: WO2023/019099
PCT Pub. Date: Feb. 16, 2023

(65) Prior Publication Data
US 2024/0358254 A1 Oct. 31, 2024

Related U.S. Application Data

(60) Provisional application No. 63/230,791, filed on Aug. 8, 2021.

(51) Int. Cl.
A61B 3/00 (2006.01)
A61B 3/10 (2006.01)
A61B 3/12 (2006.01)

(52) U.S. Cl.
CPC ............ *A61B 3/102* (2013.01); *A61B 3/0025* (2013.01); *A61B 3/1233* (2013.01)

(58) Field of Classification Search
CPC ..... A61B 3/102; A61B 3/0025; A61B 3/1233; A61B 5/0261; A61B 5/0066;
(Continued)

(56) References Cited

U.S. PATENT DOCUMENTS 10,561,392 B2 2/2020 Zhang et al.
11,202,582 B2 12/2021 Verkruijsse et al.
(Continued)

FOREIGN PATENT DOCUMENTS

EP 3884843 A1 9/2021

OTHER PUBLICATIONS

Ferris, Natalie G., et al. "Forward multiple scattering dominates speckle decorrelation in whole-blood flowmetry using optical coherence tomography." Biomedical optics express 11.4 (2020): 1947-1966.
(Continued)

*Primary Examiner* — Henry Duong
(74) *Attorney, Agent, or Firm* — QUARLES & BRADY LLP

(57) ABSTRACT

An apparatus for measuring a blood flow parameter in a blood vessel, including: an interferometric data collection apparatus including a light source and a sensor coupled to a controller, the controller being configured to: direct the light source toward a proximal side of a blood vessel; obtain interferometric data from a tissue adjacent to and outside of a distal side of the blood vessel opposite the proximal side; determine a signal modulation rate based on the interferometric data; and estimate a blood flow parameter in the blood vessel based on the signal modulation rate.

24 Claims, 11 Drawing Sheets

(58) Field of Classification Search
CPC ....... A61B 3/1025; A61B 3/12; A61B 3/1241;
A61B 3/14; A61B 3/145; G01B 9/02091
USPC ....................................................... 351/206
See application file for complete search history.

(56) References Cited

U.S. PATENT DOCUMENTS

| | | |
|---|---|---|
| 2016/0360978 A1 | 12/2016 | Chen et al. |
| 2020/0121182 A1 | 4/2020 | Guevara-Torres et al. |
| 2021/0030284 A1* | 2/2021 | Zhou .................... A61B 5/0261 |

OTHER PUBLICATIONS

Lee, Jonghwan, et al. "Dynamic light scattering optical coherence tomography." Optics express 20.20 (2012): 22262-22277.

Nam, Ahhyun Stephanie, Boy Braaf, and Benjamin J. Vakoc. "Using the dynamic forward scattering signal for optical coherence tomography based blood flow quantification." Optics letters 47.12 (2022): 3083-3086.

Uribe-Patarroyo, Néstor, and Brett E. Bouma. "Velocity gradients in spatially resolved laser Doppler flowmetry and dynamic light scattering with confocal and coherence gating." Physical Review E 94.2 (2016): 022604.

International Search Report in International Application No. PCT/US2022/074653; received on Nov. 8, 2022.

Extended European Search Report in European Application No. 22856741.8; received on May 19, 2025.

* cited by examiner

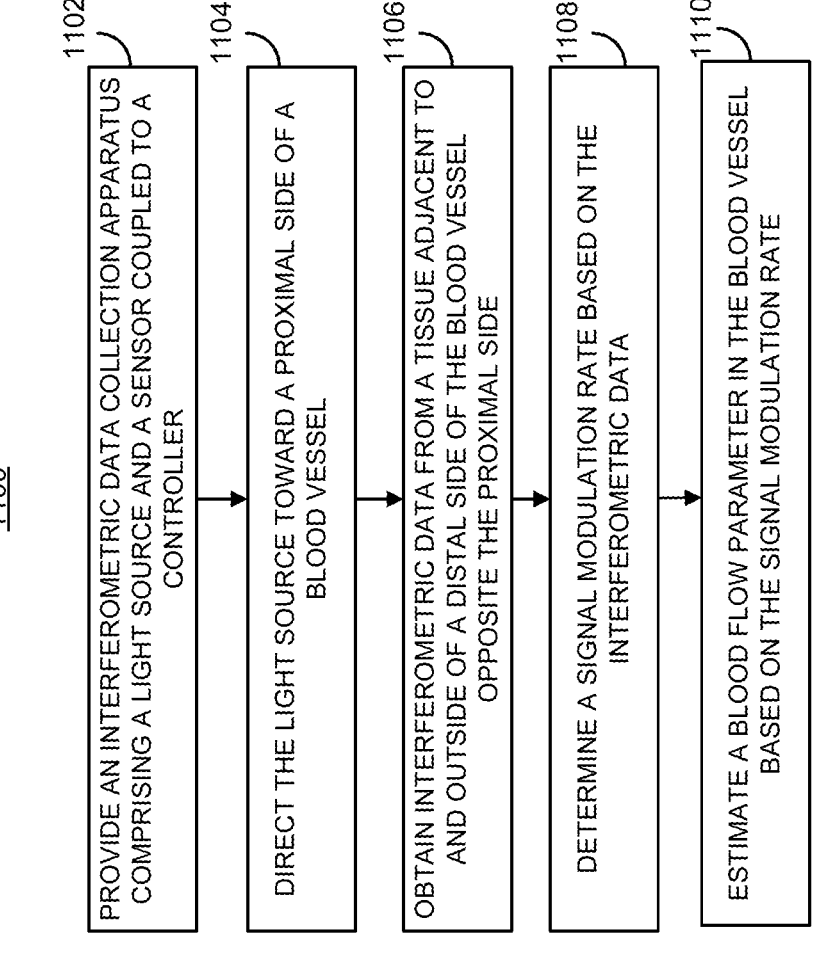

1100

PROVIDE AN INTERFEROMETRIC DATA COLLECTION APPARATUS COMPRISING A LIGHT SOURCE AND A SENSOR COUPLED TO A CONTROLLER
1102

DIRECT THE LIGHT SOURCE TOWARD A PROXIMAL SIDE OF A BLOOD VESSEL
1104

OBTAIN INTERFEROMETRIC DATA FROM A TISSUE ADJACENT TO AND OUTSIDE OF A DISTAL SIDE OF THE BLOOD VESSEL OPPOSITE THE PROXIMAL SIDE
1106

DETERMINE A SIGNAL MODULATION RATE BASED ON THE INTERFEROMETRIC DATA
1108

ESTIMATE A BLOOD FLOW PARAMETER IN THE BLOOD VESSEL BASED ON THE SIGNAL MODULATION RATE
1110

FIG. 11

USING THE DYNAMIC FORWARD SCATTERING SIGNAL FOR OPTICAL COHERENCE TOMOGRAPHY BASED FLOW QUANTIFICATION

CROSS-REFERENCE TO RELATED APPLICATIONS

The present application represents the U.S. national stage entry of International Patent Application Ser. No. PCT/US2022/074653, filed on Aug. 8, 2022, which is based on and claims priority from U.S. Patent Application Ser. No. 63/230,791, filed on Aug. 8, 2021, the entire disclosure of which is incorporated herein by reference.

STATEMENT REGARDING FEDERALLY SPONSORED RESEARCH

This invention was made with government support under grant number P41EB015903 awarded by the National Institutes of Health/National Institute of Biomedical Imaging and Bioengineering. The government has certain rights in the invention.

BACKGROUND

Optical coherence tomography (OCT) can be used to quantify blood flow within individual vessels. Numerous approaches have been described which are generally based on a common principle, namely the movement of scatterers (e.g. red blood cells (RBCs)) which induces a modulation of the OCT signal, where the rate of that modulation is proportional to the flow speed of the scatterers. OCT flowmetry systems are therefore designed to first measure the rate of signal modulation (by some metric) and second relate this rate back to a flow parameter (e.g., speed or volumetric flow). Nevertheless, there are challenges in each of these steps that must be overcome to realize robust OCT-based flowmetry.

SUMMARY OF THE INVENTION

Accordingly, new systems, methods, and media for measuring a flow parameter are desirable.

Vascular and hemodynamic abnormalities have been closely associated with pathogenesis and progression of many ocular diseases. Consequently, numerous methods have been proposed to qualitatively visualize the vasculature and use 'vascular density' as a surrogate measure of perfusion. However, no existing technique can provide robust measurement of the blood flow through the vasculature.

We have observed that OCT time-series measurements in the static tissues underlying blood vessels have dynamic characteristics that can be analyzed and related to the actual blood flow. The approach is named "dynamic forward scattering" (DFS), as the optical signals we focus on are modulated by the photons that are forward scattered from red blood cells in a blood vessel. Through various experiments and developments, we have obtained data confirming that these signals allow a robust measure of blood flow, free from the artifacts that impede direct analysis of the signals coming from inside the vessels via single back-scattering.

We note that the DFS approach is uniquely advantageous for flow assessment in the choroid, which is characterized by extremely weak signals when probed with OCT. The sclera, a layer below the choroid, is highly scattering, homogenous, and nearly avascular, which makes the disclosed procedures particularly well suited for use with this tissue. The signal from the sclera is brighter than the choroidal vessel lumens, and the imaging penetration can be several hundred microns. This has two consequences when we analyze the OCT signals in the sclera to calculate the blood flow in the choroid: (i) the analyzed sclera voxels can have a higher signal-to-noise ratio (SNR) than choroidal blood voxels, and (ii) there can be more voxels available for analysis.

The approach disclosed herein enables OCT-based blood flowmetry by focusing on the dynamics of the signals captured by forward-scattered light. By contrast, all existing OCT-flowmetry methods, to our knowledge, focus on the OCT measurements of the single back-scattering within a blood vessel. We developed the concept and the framework to utilize all available measurements from both inside and outside of the vessel lumen (in particular, under the vessels) that contain information on the blood flow, in order to provide a robust estimate of the blood flow.

Embodiments of the disclosed procedures may be used as a part of a protocol to assess blood flow in the posterior eye using any optical coherence tomography system. Embodiments of the procedure can be implemented on conventional OCT systems such as those that are used in clinics. The acquisition protocols (in the software) can be modified to acquire the data needed for quantitative blood flow assessment and various analyses can be performed in post-processing.

Accordingly, in various embodiments, the disclosure provides an apparatus for measuring a blood flow parameter in a blood vessel. The apparatus may include an interferometric data collection apparatus including a light source and a sensor coupled to a controller. The controller may be configured to: direct the light source toward a proximal side of a blood vessel; obtain interferometric data from a tissue adjacent to and outside of a distal side of the blood vessel opposite the proximal side; determine a signal modulation rate based on the interferometric data; and estimate a blood flow parameter in the blood vessel based on the signal modulation rate.

In some embodiments, the signal modulation rate may include a decorrelation rate. In other embodiments, the signal modulation rate may include or be based upon a measurement of the signal's temporal cross-correlation or temporal covariance. In certain embodiments, the light source may be directed in an orientation that is substantially orthogonal to a central axis of the blood vessel. The central axis of the vessel is generally parallel to the axis along which material in the vessel (e.g. blood) is flowing.

In certain embodiments, the interferometric data collection apparatus may include an optical coherence tomography (OCT) apparatus. Thus the controller, when obtaining interferometric data, may be further configured to: obtain OCT data from the tissue adjacent to and outside of the distal side of the blood vessel opposite the proximal side, and the controller, when determining a signal modulation rate based on the interferometric data, may be further configured to: determine the signal modulation rate based on the OCT data.

In various embodiments, the OCT data may be based on forward-scattering of light from the light source by the flowing blood into the tissue adjacent to and outside of the distal side of the blood vessel. Thus the controller, when estimating a blood flow parameter in the blood vessel, may be further configured to: estimate the blood flow parameter in the blood vessel, wherein the blood flow parameter is based on accumulated flow throughout the blood vessel; that is, the blood flow parameter may not measure the depth-resolved flow within a vessel.

In some embodiments, the blood vessel and the tissue may be located in a retina of a subject. In certain embodiments, the tissue may include at least one of scleral tissue or retinal pigment epithelium (RPE) tissue adjacent to and outside of the distal side of the blood vessel.

In particular embodiments, the blood flow parameters include at least one of flow speed (e.g., in mm/sec), velocity (e.g., in mm/sec with an associated spatial direction), or flux (e.g., in mL/sec or in the number of RBCs passing through the imaging beam per second).

In various embodiments, the controller, when obtaining interferometric data from a tissue adjacent to and outside of a distal side of the blood vessel opposite the proximal side, may be further configured to: obtain back-scattered interferometric data from inside the blood vessel, and, when determining a signal modulation rate based on the interferometric data, may be further configured to: determine a back-scattered signal modulation rate based on the back-scattered interferometric data, and, when estimating a blood flow parameter in the blood vessel based on the signal modulation rate, may be further configured to: estimate the blood flow parameter in the blood vessel based on the back-scattered signal modulation rate. Accordingly, in such embodiments the back-scattered interferometric data may be used, e.g. along with the forward-scattered interferometric data, to estimate the blood flow parameter.

In some embodiments, the disclosure provides a method for measuring a blood flow parameter in a blood vessel, including: providing an interferometric data collection apparatus including a light source and a sensor coupled to a controller; directing, using the controller, the light source toward a proximal side of a blood vessel; obtaining, using the controller, interferometric data from a tissue adjacent to and outside of a distal side of the blood vessel opposite the proximal side; determining, using the controller, a signal modulation rate based on the interferometric data; and estimating, using the controller, a blood flow parameter in the blood vessel based on the signal modulation rate.

In certain embodiments, determining a signal modulation rate may further include: determining a decorrelation rate based on the interferometric data, and estimating a blood flow parameter in the blood vessel may further include: estimating the blood flow parameter in the blood vessel based on the decorrelation rate.

In various embodiments, directing the light source toward a proximal side of a blood vessel may further include: directing the light source toward a proximal side of the blood vessel in an orientation that is substantially orthogonal to a central axis of the blood vessel.

In particular embodiments, the interferometric data collection apparatus may include an optical coherence tomography (OCT) apparatus, and obtaining interferometric data may further include: obtaining OCT data from the tissue adjacent to and outside of the distal side of the blood vessel opposite the proximal side, and determining a signal modulation rate based on the interferometric data may further include: determining the signal modulation rate based on the OCT data. In some embodiments, the OCT data may be based on forward-scattering of light from the light source by the flowing blood into the tissue adjacent to and outside of the distal side of the blood vessel. In certain embodiments, estimating a blood flow parameter in the blood vessel further may further include: estimating the blood flow parameter in the blood vessel, wherein the blood flow parameter is based on accumulated flow throughout the blood vessel.

In various embodiments, the blood vessel and the tissue may be located in a retina of a subject. In some embodiments, the tissue may include at least one of scleral tissue or retinal pigment epithelium (RPE) tissue adjacent to and outside of the distal side of the blood vessel.

In some embodiments, the blood flow parameters may include at least one of flow speed (e.g., in mm/sec), velocity (e.g., in mm/sec with an associated spatial direction), and flux (e.g., in mL/sec or in the number of RBCs passing through the imaging beam per second).

In certain embodiments, obtaining interferometric data from a tissue adjacent to and outside of a distal side of the blood vessel opposite the proximal side may further include: obtaining back-scattered interferometric data from inside the blood vessel, determining a signal modulation rate based on the interferometric data may further include: determining a back-scattered signal modulation rate based on the back-scattered interferometric data, and estimating a blood flow parameter in the blood vessel based on the signal modulation rate may further include: estimating the blood flow parameter in the blood vessel based on the back-scattered signal modulation rate.

In various embodiments, the disclosure provides an apparatus for measuring a flow parameter in a vessel, including: an interferometric data collection apparatus including a light source and a sensor coupled to a controller. The controller may be configured to: direct the light source toward a proximal side of a vessel; obtain interferometric data from a sample adjacent to and outside of a distal side of the vessel opposite the proximal side; determine a signal modulation rate based on the interferometric data; and estimate a flow parameter in the vessel based on the signal modulation rate.

In some embodiments, the signal modulation rate may include a decorrelation rate. In certain embodiments, the light source may be directed in an orientation that is substantially orthogonal to a central axis of the vessel.

In particular embodiments, the interferometric data collection apparatus may include an optical coherence tomography (OCT) apparatus, and the controller, when obtaining interferometric data, may be further configured to: obtain OCT data from the sample adjacent to and outside of the distal side of the vessel opposite the proximal side, and, when determining a signal modulation rate based on the interferometric data, may be further configured to: determine the signal modulation rate based on the OCT data. In some embodiments, the OCT data may be based on forward-scattering of light from the light source by material flowing in the vessel into the sample adjacent to and outside of the distal side of the vessel. In certain embodiments, the controller, when estimating a flow parameter in the vessel, may be further configured to: estimate the flow parameter in the vessel, wherein the flow parameter may be based on accumulated flow throughout the vessel.

In some embodiments, the vessel and the sample may be located in a living tissue. In other embodiments, the vessel and the sample may be located within a biological tissue that is prepared ex vivo or in vitro such as a tumor spheroid. In other embodiments, the vessel and the sample may be located within an engineering construct such as a flow phantom or a microfluidic platform.

In various embodiments, the flow parameters may include at least one of flow speed (e.g., in mm/sec), velocity (e.g., in mm/sec with an associated spatial direction), and flux (e.g., in mL/sec or in the number of RBCs passing through the imaging beam per second).

In particular embodiments, the controller, when obtaining interferometric data from a sample adjacent to and outside of a distal side of the vessel opposite the proximal side, may be further configured to: obtain back-scattered interferometric data from inside the vessel, when determining a signal modulation rate based on the interferometric data, may be further configured to: determine a back-scattered signal modulation rate based on the back-scattered interferometric data, and when estimating a flow parameter in the vessel based on the signal modulation rate, may be further configured to: estimate the flow parameter in the vessel based on the back-scattered signal modulation rate.

In various embodiments, the disclosure may provide a method for measuring a flow parameter in a vessel, including: providing an interferometric data collection apparatus including a light source and a sensor coupled to a controller; directing, using the controller, the light source toward a proximal side of a vessel; obtaining, using the controller, interferometric data from a sample adjacent to and outside of a distal side of the vessel opposite the proximal side; determining, using the controller, a signal modulation rate based on the interferometric data; and estimating, using the controller, a flow parameter in the vessel based on the signal modulation rate.

In some embodiments, determining a signal modulation rate may further include: determining a decorrelation rate based on the interferometric data, and estimating a flow parameter in the vessel may further include: estimating the flow parameter in the vessel based on the decorrelation rate.

In certain embodiments, directing the light source toward a proximal side of a vessel may further include: directing the light source toward a proximal side of the vessel in an orientation that is substantially orthogonal to a central axis of the vessel.

In particular embodiments, the interferometric data collection apparatus may include an optical coherence tomography (OCT) apparatus, and obtaining interferometric data may further include: obtaining OCT data from the sample adjacent to and outside of the distal side of the vessel opposite the proximal side, and determining a signal modulation rate based on the interferometric data may further include: determining the signal modulation rate based on the OCT data. In certain embodiments, the OCT data may be based on forward-scattering of light from the light source by material flowing in the vessel into the sample adjacent to and outside of the distal side of the vessel. In various embodiments, estimating a flow parameter in the vessel may further include: estimating the flow parameter in the vessel, wherein the flow parameter is based on accumulated flow throughout the vessel.

In some embodiments, the vessel and the sample may be located in a living tissue. In other embodiments, the vessel and the sample may be located within a biological tissue that is prepared ex vivo or in vitro such as a tumor spheroid. In other embodiments, the vessel and the sample may be located within an engineering construct such as a flow phantom or a microfluidic platform.

In particular embodiments, the flow parameters may include at least one of flow speed (e.g., in mm/sec), velocity (e.g., in mm/sec with an associated spatial direction), and flux (e.g., in mL/sec or in the number of RBCs passing through the imaging beam per second).

In certain embodiments, obtaining interferometric data from a sample adjacent to and outside of a distal side of the vessel opposite the proximal side may further include: obtaining back-scattered interferometric data from inside the vessel, determining a signal modulation rate based on the interferometric data may further include: determining a back-scattered signal modulation rate based on the back-scattered interferometric data, and estimating a flow parameter in the vessel based on the signal modulation rate may further include: estimating the flow parameter in the vessel based on the back-scattered signal modulation rate.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 11 shows an example of a process for measuring a flow parameter in accordance with some embodiments of the disclosed subject matter.

DETAILED DESCRIPTION

Figure 1:
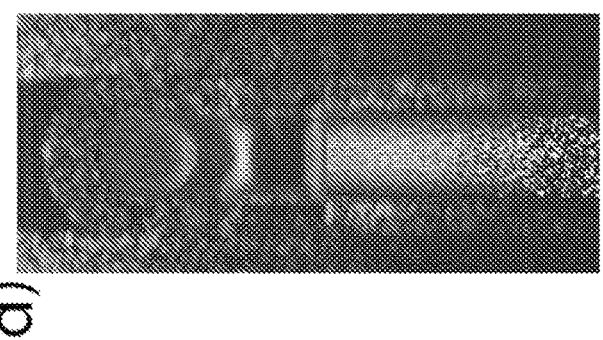
FIG. 1, panel (a) shows the geometry of signals dynamically back-scattered (DBS) and dynamically forward-scattered (DFS) from a vessel. Panel (b) shows a diagram of a flow phantom, where the inner diameter of the polystyrene flow tube is 125 µm, and a Teflon static scatterer is placed below the tube. Panel (c) shows an OCT structure image of the tube phantom, where marked areas indicate the DBS voxels that are prone to artifacts caused by axial-gradient effect (yellow) and multiple scattering (cyan). Panel (d) shows an estimated decorrelation rate $(\hat{\rho})$ (represented by colors on a viridis scale where blue is the lowest value and yellow is the highest value) for each voxel within DBS and DFS regions is overlaid on the structure image. For these data, the pump flow rate is set at 50 µL/min and the flow angle is $\alpha=96.83°$.
Figure 1:
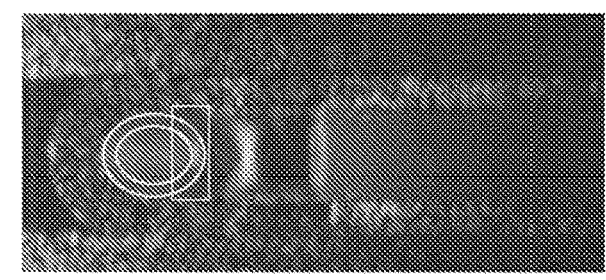
Figure 1:
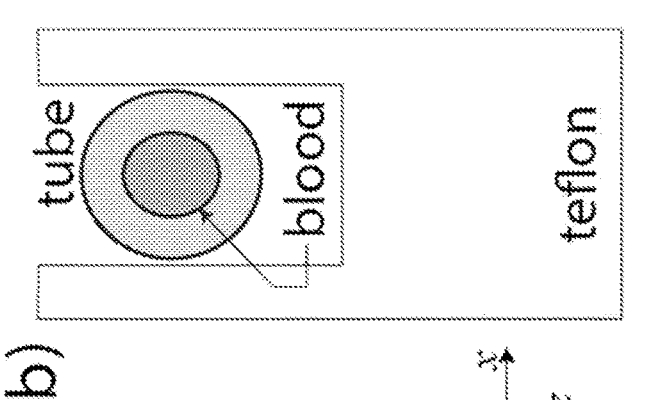
Figure 1:
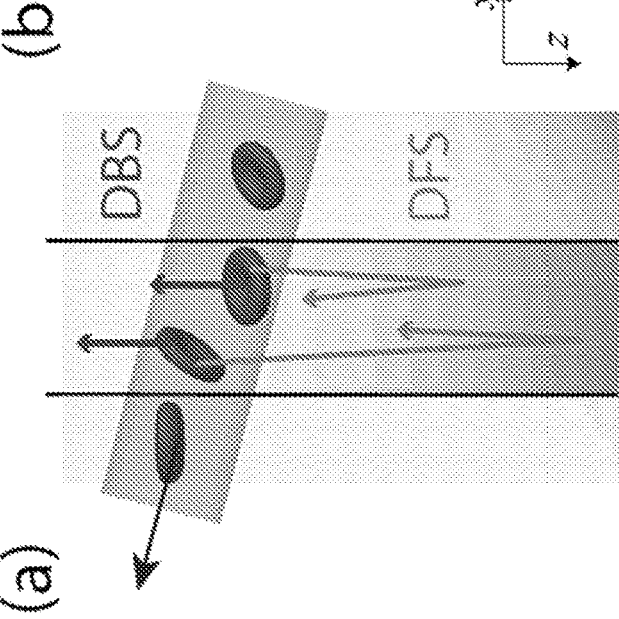

In accordance with some embodiments of the disclosed subject matter, mechanisms (which can include systems, methods, and media) for measuring a flow parameter are provided.

To the knowledge of the inventors, all existing optical coherence tomography approaches for quantifying blood flow (whether Doppler-based or decorrelation-based) analyze light that is back-scattered by materials such as moving red blood cells (RBCs). The present application discloses the advantages of instead basing these measurements on light that is forward-scattered by RBCs, i.e., by looking at the signals back-scattered from below (i.e. on the distal side of) the vessel. We show experimentally herein that flowmetry based on forward-scattering is insensitive to vessel orientation for vessels that are approximately orthogonal to the imaging beam. We further provide proof-of-principle demonstrations of dynamic forward-scattering (DFS) flowmetry in human retinal and choroidal vessels. Nevertheless, while many of the examples provided herein are based on data obtained from blood vessels within the posterior eye, the disclosed procedures can be carried out on a wide variety of tissues and materials including skin, brain, gastrointestinal tissues, nerves, and precancerous and cancerous lesions.

Optical coherence tomography (OCT) can be used to quantify blood flow within individual vessels. Numerous approaches have been described, but all are based on a common principle, namely the movement of scatterers (e.g. red blood cells (RBCs)) which induces a modulation of the OCT signal where the rate of that modulation is proportional to the flow speed of the scatterers. OCT flowmetry systems are therefore designed to first measure the rate of signal modulation (by some metric) and second relate this rate back to a flow parameter (e.g., speed or volumetric flow). There are challenges in each of these steps that must be overcome to realize robust OCT-based flowmetry.

In this work, we disclose a strategy to overcome a central challenge in the second step: the calculation of flow from a measured signal modulation rate. It has been established that flow calculations may be unreliable for vessels that are oriented approximately orthogonal to the OCT beam (Doppler angle α≈90°), which is especially problematic for measurements of vessels in the retina which are for the most part orthogonal to the OCT beam. A root cause of this poor reliability is the highly anisotropic phase response of back-scattering to axial and transverse motion. Axial motion on the scale of half of the light wavelength induces a full $2\pi$ phase modulation, while transverse motion must be on the order of the imaging resolution, typically 10-20 μm, to achieve a similar expected phase response. This is, of course, why Doppler-based methods, which by definition operate on the signal phase, measure axial motion. Less evident is how this may affect decorrelation-based methods, including decorrelation-based methods that operate on the OCT intensity signal. Here, it is shown that the variation in phase response arising from intravoxel gradients of axial motion leads to a rapid decorrelation of the OCT signal. This is true regardless of whether one operates on the complex-valued or intensity signals. While the disclosed examples are directed at determinations of the decorrelation rate, in various embodiments other types of analyses can be performed on the flow related DFS signal such as power spectrum analysis or statistical inference based on a model. In other embodiments, the signal modulation rate may include or be based upon a measurement of the signal's temporal cross-correlation or temporal covariance.

When the known axially-biased methods are applied to vessels with Doppler angles near 90°, the signal modulation rate disproportionally measures the relatively small axial component of the velocity and the flow calculation from signal modulation rate becomes unreliable because the signal modulation has large dependence on the relatively small axial component of the velocity. To calculate the total flow using these axially-biased methods, one needs to scale up the measurement using a geometric factor. Without precise knowledge of α, the resulting calculated total flow is unreliable. In various embodiments, the disclosed procedures can be used to measure a variety of flow parameters (e.g. blood flow parameters) including flow speed (e.g., in mm/sec), velocity (e.g., in mm/sec with an associated spatial direction), and flux (e.g., in mL/sec or in the number of RBCs passing through the imaging beam per second).

If we could either make the response to scatterer motion isotropic or flip the anisotropy toward transverse motion, then the calculation of total flow would be much more stable for vessels with Doppler angles near 90°. It turns out that light that is forward-scattered by a moving scatterer has the latter property. This can be seen in the conceptual illustration of the photon paths of dynamically back-scattered (DBS) and dynamically forward-scattered (DFS) light, illustrated in FIG. 1(a). Of course, OCT is a reflective imaging technique, so we cannot measure the DFS light directly. However, we can indirectly measure DFS by looking at the signals that are back-scattered from below the vessel and have necessarily traveled twice through the vessel. Thus, to the extent that the light source is directed to a proximal side of the vessel, the interferometric data is obtained from a tissue or other material in a region that is adjacent to (and outside of) a distal side of the vessel opposite the proximal side.

To characterize the properties of DFS and its fidelity as a measure of superjacent vessel flow, we constructed a blood flow phantom as shown in FIGS. 1(b) and 1(c) (all measurements in this work use blood as the exemplary flow media). We characterized the decorrelation rate of the signals in the voxels below the flow tube (FIG. 1(d)). To quantify the decorrelation rate, we modeled the autocorrelation/autocovariance of the DFS signal as $$g^{(1)}(\tau) \propto e^{-\rho^2 \tau^2} \qquad (1)$$

where T is the delay between measurements. The function $g^{(1)}(\tau)$ is the complex autocorrelation function. We estimated the value of $\rho$ using complex-valued OCT data. Briefly, we used a maximum-likelihood-based statistical framework. A method that instead fits the complex autocorrelation function to the calculated autocorrelation coefficients of the measurement could also be used, i.e., the DFS approach is not tied to a specific analysis framework.

The decorrelation rate can be measured by calculating the autocovariance of the measured temporal signal and fitting these autocovariance data to the expression in Eq. (1) to find the value of $\rho$ that yields the best fit. Numerical methods such as optimization can be used to perform this fitting. The model provided by Eq. (1) can be modified to have a different functional form on a decorrelation rate parameter $\rho$ or a different functional form on the delay $\tau$. The measured data can be complex-valued, in which case the autocovariance is a complex-valued output. Alternatively, the amplitude or amplitude squared of the measurement data (both real-valued) can be used to calculate a real-valued autocovariance measurement. Accordingly, decorrelation or signal modulation models such as those used in Eq. (1) can be written for real-valued or complex-valued measurements and the appropriate model can be used in the fitting.

Additional metrics can be calculated from the time-series measurements acquired outside of the vessel in order to estimate flow properties. These include a power spectral analysis, where power that is localized to lower RF frequencies is associated with slower flow, while power that extends more broadly across RF frequencies is associated with faster flow. Other techniques and methods that measure the dynamic properties of the time-series OCT measurements and that are known to those skilled in the art can additionally be used.

Further, we note that the decorrelation analysis in this application refers to the generalized measurement of how rapidly a single fluctuates and is not limited to a specific methodology and definition of the decorrelation or decorrelation rate.

It is important to highlight that Eq. (1) is an assumed statistical model for the DFS signals. While there have been many efforts to define a statistical model for DBS signals, there is no such body of work for DFS signals. Therefore, it is possible that the DFS signal follows a different functional dependence on T than that of Eq. (1). In addition, even if we assume Eq. (1) is the correct statistical model for the DFS signal, it is not known how $\rho$ is related to the flow properties of the superjacent vessel. For example, $\rho$ might be proportional to the peak velocity, or instead, it might be related to the RBC flux. These are critical questions to be answered in the broader development of a DFS-based flow quantification strategy and will likely require significant effort. Here, we sought to confirm the motivating principle behind the approach—that the DFS decorrelation rate is insensitive to a around $\alpha=90°$. An assumed model is sufficient for this goal.

Imaging was performed using an M-mode B-scan protocol wherein 128 A-lines were recorded at each of 100 positions spanning 300 µm (100 (x) by 128 (t) A-lines per frame). Ten repeated B-scan frames were acquired at each location. Imaging was performed at 19 different locations, each providing a different Doppler angle from 80° to 100°.

We calculated an estimate of $\rho$, denoted by $\hat{\rho}$, for each voxel within the DBS region (within the tube) and the DFS region (below the tube). All data in this work were acquired using a swept-source OCT system (center wavelength 1060 nm, 100 kHz A-line rate). Apparatus and procedures for developing and using the OCT system, flow phantom, beam scan protocols, and the calibration and removal of bulk-motion are known to those skilled in the art.

DFS Decorrelation Rates are Insensitive to Doppler Angle

FIG. 2(a) shows exemplary frames of the estimated decorrelation rate coefficient $\hat{\rho}$ for both the DBS and DFS regions overlaid on the intensity frames and for Doppler angles of 80.8° and 89.2°. The flow rate for both measurements was 60 µl/min. Note the velocity gradient contribution to the decorrelation rate in the DBS signal at 80.8°. The increased decorrelation in the lower region of the lumen is presumed to be caused by multiple-scattering (in effect, DFS), which is discussed further below. In FIG. 2(a), it is clear that the Doppler angle affects $\hat{\rho}$ in the DBS region but has less impact on the DFS region.

Figure 6:
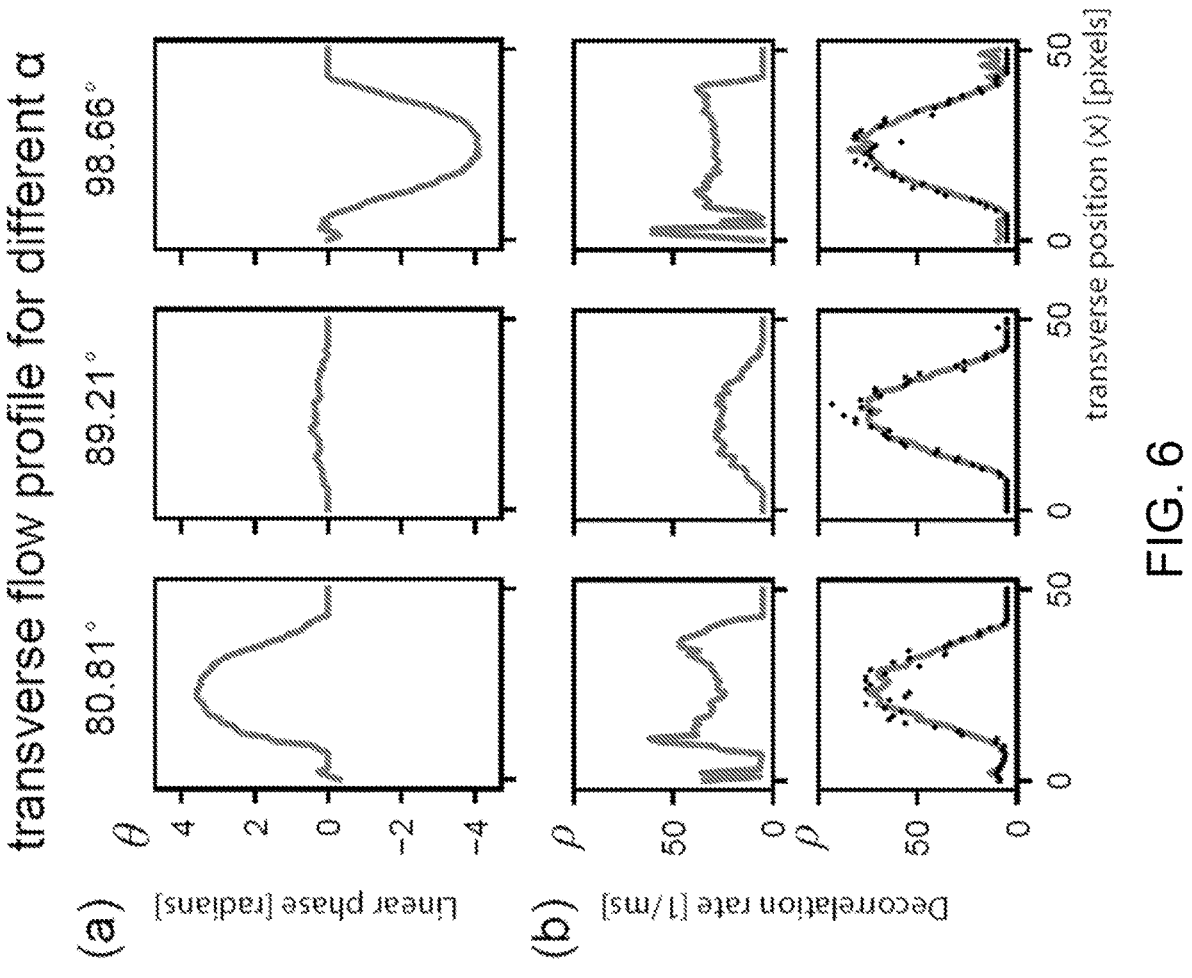
FIG. 6 shows a linear phase (Doppler) profile inside the tube, depicting a transverse flow profile for different flow angles. Panel (a) shows the linear Doppler phase showing the axial flow speed, where the Doppler phase is not affected by the velocity gradient effect at the edge of the tube. Panel (b) shows the decorrelation rate inside the tube (top) and in the DFS (bottom). The first two columns show the same plot as shown in FIG. 2, panel (b).

To more clearly visualize how the Doppler angle affects the DBS and DFS signals, transverse profiles of $\hat{\rho}$ are shown in FIG. 2(b) for the 80.8° (left column) and 89.2° (right column) measurements and at the indicated lines in the DBS (upper row) and DFS (lower row) regions. For the DFS signal, the transverse profiles of $\hat{\rho}$ are at least approximately parabolic and do not change between the two Doppler angles. For reference, the Doppler linear phase shifts for these measurements are shown in FIG. 6.

To quantify the decorrelation properties across the 19 flow angles, we calculated the average $\hat{\rho}$ in the ROIs defined in FIG. 2(c) for a fixed flow rate of 60 µl/min. Two ROIs are defined for the DBS region, one equal to the full lumen and one that excludes (i) edges where velocity gradients are highest and (ii) the lower tube region wherein multiple-scattering is significant. The DFS ROI covers a large region below the tube (purple). FIG. 2(d) presents these measurements normalized to that obtained at a Doppler angle of 90°. Note the strong quadratic dependence of decorrelation on Doppler angle for the full lumen DBS ROI, and a reduced quadratic dependence on Doppler angle for the reduced tube ROI. The DFS signal shows no evidence of a quadratic dependence on the Doppler angle. A minimal linear dependence on Doppler angle is seen, but this is more likely to be a measurement artifact than a true response. We conclude this because we do not know of a mechanism which would create an asymmetry around a Doppler angle of 90° and because a similar linear trend is observed in the DBS measurements.

DFS Decorrelation Rates Scale Linearly with Flow Speed

Figure 7:
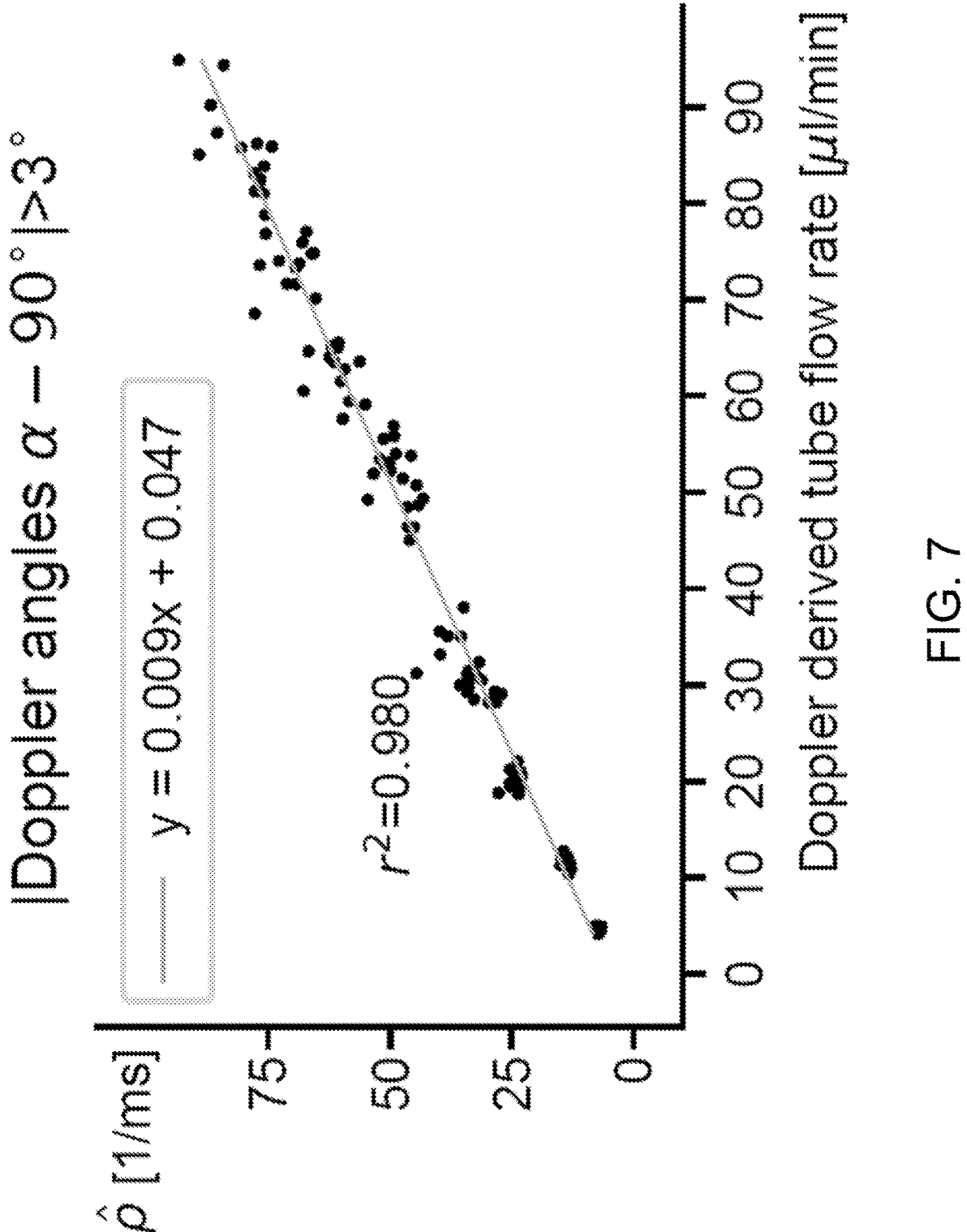
FIG. 7 shows a linear trend of the flow rate at various flow angles, where DFS decorrelation rates (averaged over the DFS ROI in FIG. 2, panel (c)) for all flow angles outside a 3° deviation from α=90°. The horizontal axis is the Doppler-derived flow rate.

Next, we used the flow phantom to confirm that the decorrelation rate in the DFS region varies linearly with changes in flow speed, holding all other properties (e.g., tube geometry) constant. Using a Doppler angle of 83.5°, we calculated the average $\hat{\rho}$ in the DFS ROI for varying pump flow settings. These measures are plotted in FIG. 3(a) as a function of the flow rate derived by a Doppler analysis of the DBS signal ($F_{Doppler}$). As expected, the trend is strongly linear. There is also a small y-axis offset. We repeated this analysis for all Doppler angles greater than 3° from 90° (to ensure robust Doppler measurements in the DBS signal), and observed the same trend with nearly identical slope and offsets (FIG. 7). The cause of the nonzero y-axis intercept is not known; possible sources include Brownian motion and measurement noise.

Figure 2:
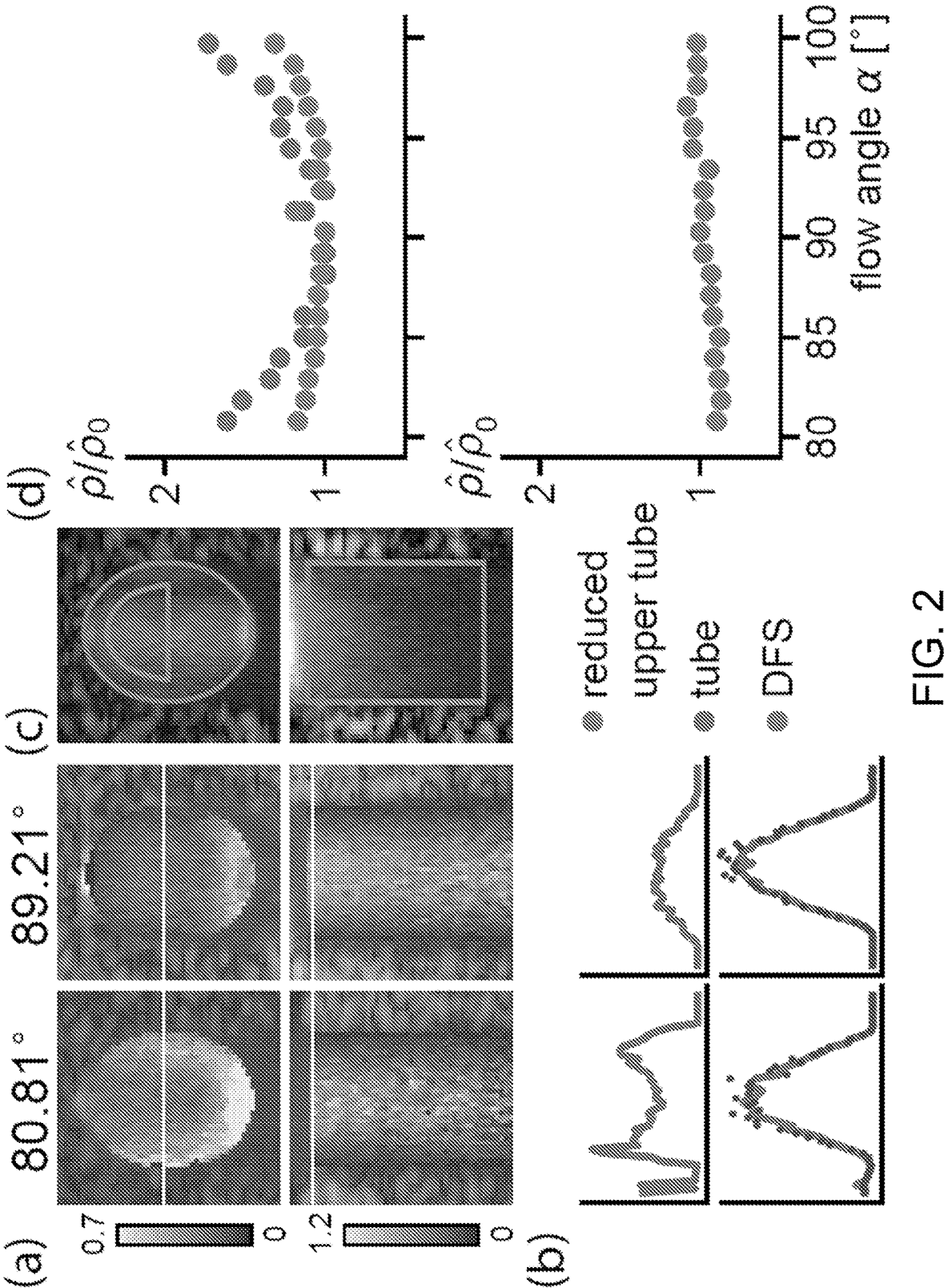
FIG. 2, panel (a) shows visualization of DBS and DFS decorrelation estimates $(\hat{\rho})$ for two Doppler angles. Panel (b) shows transverse $\hat{\rho}$ profiles at locations marked by white lines in panel (a). Panel (c) shows the ROI for average decorrelation rate. Panel (d) shows average $\hat{\rho}$ (normalized to $\hat{\rho}_0$, the value at a Doppler angle of 90°) within the two DBS ROIs (full lumen, and inner 66% diameter of the upper half of the tube, upper plot), and the DFS ROI (lower plot).
Figure 3:
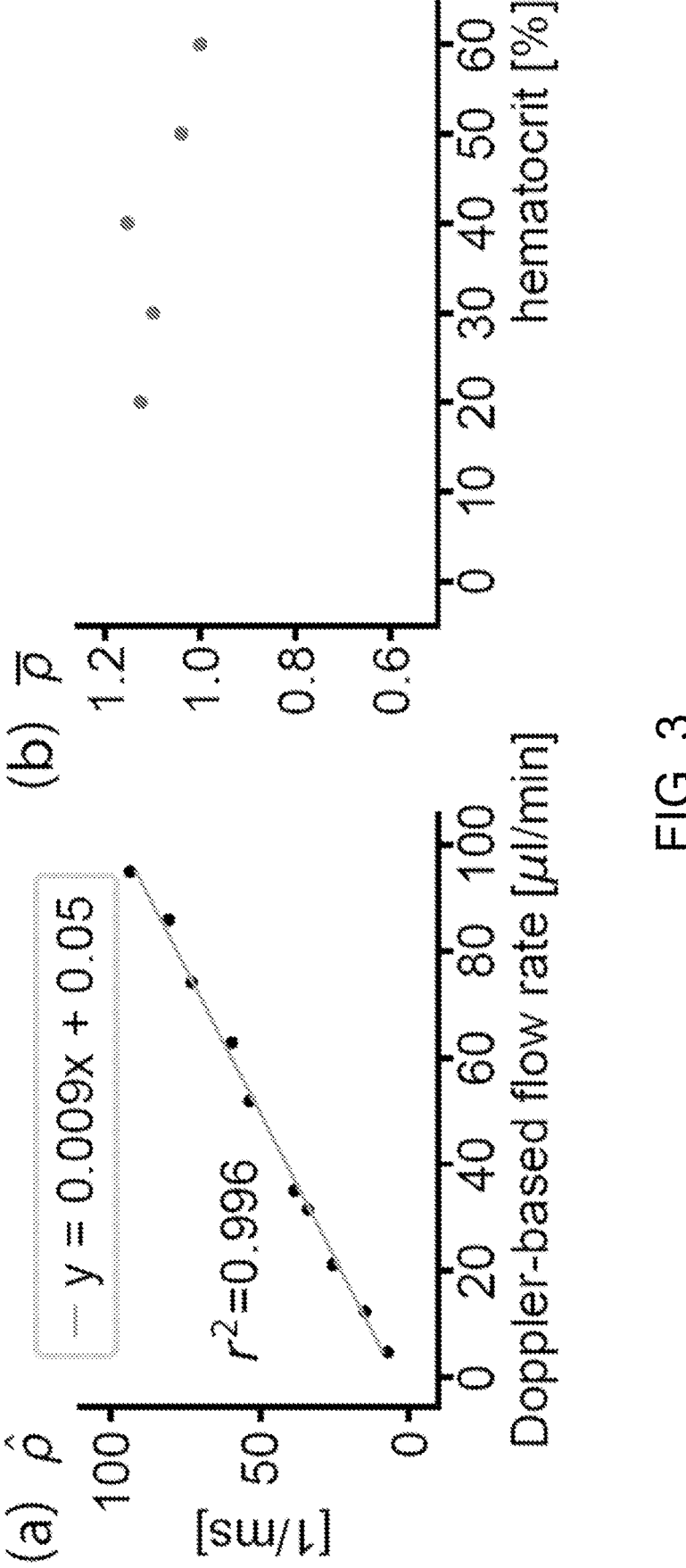
FIG. 3, panel (a) shows DFS decorrelation rates $(\hat{\rho},$ averaged over the DFS ROI) plotted against the Doppler-derived flow rate in the tube. Panel (b) shows $\hat{\rho}$ normalized to the 60% hematocrit level.

DFS Decorrelation Rates are More Strongly Associated with Flow Speed than RBC Flux As previously stated, a statistical (autocorrelation or auto-covariance) model of the DFS signal has not been described. Therefore, we do not know how to relate the decorrelation rate to the flow properties of the superjacent vessel. It is possible, for example, that, unlike the DBS signal, the DFS signal may depend on both the motion of the forward scattering RBCs and the number of RBCs with which the light has interacted. The latter would imply that the DFS signal measures, in part, the RBC flux. To test this, we compared $\hat{\rho}$ for various dilutions of the blood yielding hematocrit levels from 20% to 60% (FIGS. 1-3 used a hematocrit of 60%). If DFS decorrelation rates are significantly affected by RBC flux, we should see a dramatic reduction in $\hat{\rho}$ at lower hematocrit. In this analysis, we removed the effect of pump variability by normalizing $\hat{\rho}$ to the Doppler-derived flow ($F_{Doppler}$). At each hematocrit level, we averaged measurements across all Doppler angles more than 3° from 90°.

FIG. 3(*b*) presents the results. The normalized decorrelation rate ($\hat{\rho}/F_{Doppler}$), relative to that at hematocrit of 60%, are 1.126, 1.1, 1.154, 1.04, for 20, 30, 40, and 50% of hematocrit, respectively. There is no observable trend toward lower $\hat{\rho}$ for lower hematocrit. In fact, a small increase was observed for lower hematocrit, although this could be explained by secondary factors (such as the influence of hematocrit on the SNR of the DFS signal). These results do not exclude an RBC flux dependence within the DFS decorrelation rate, but they indicate that any such dependence is likely much smaller than that of flow speed.

Application to Retinal and Choroidal Vessels

Figure 4:
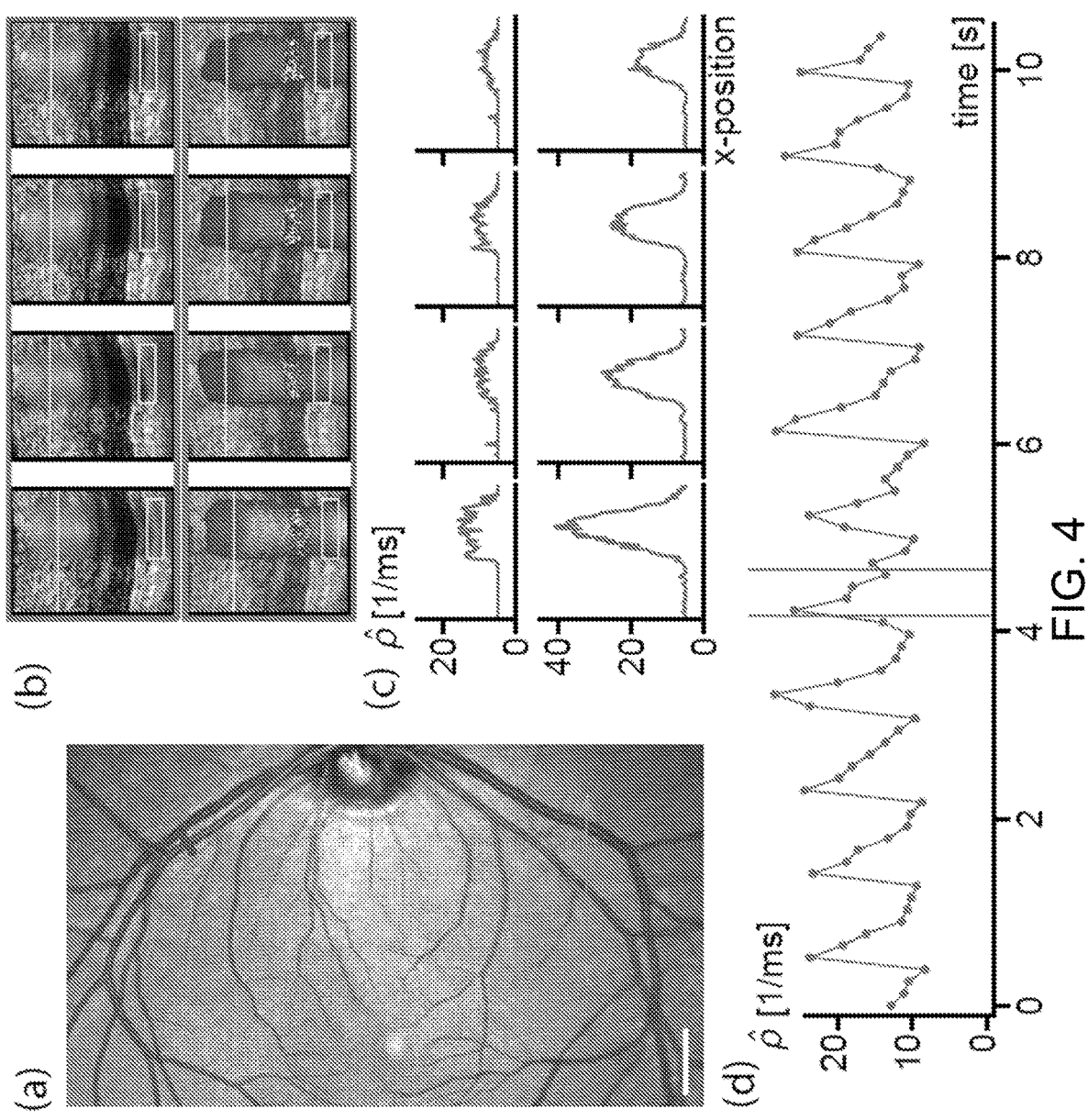
FIG. 4, panel (a) shows a scanning laser ophthalmoscope image of a retina indicating the scan locations used to measure DFS signals below a retinal vessel (blue line, upper portion of image) and across multiple choroidal vessels (magenta line, lower portion of image). Scale bar=1 mm. Panel (b) shows filmstrips of the structure (top) and decorrelation rate parameter $(\hat{\rho})$ (bottom). Panel (c) shows transverse flow profiles across the DBS (top) and DFS (bottom) ROIs. Panel (d) shows the average value of $\hat{\rho}$ within the DFS ROI which is plotted over time and shows cardiac pulsatility. The vertical red lines bracket the temporal period containing the four time-points (indicated as blue dots between the red lines) at which flow cross-sections are presented in panel (b).

Finally, we demonstrate that DFS-based techniques can be applied to the larger retinal and choroidal vessels in human subjects. First, we measured the decorrelation rate associated with the DFS signal below a retinal vessel as indicated in FIG. 4(*a*) (location indicated by the short blue line in the upper portion of the image). Because the retinal pigment epithelium (RPE) is avascular and highly scattering, we used this tissue as the static reporter of the DFS signal. Data were acquired with the same M-mode B-scan protocol used for flow phantom imaging except that B-scans were repeated over approximately 10 seconds to capture pulsatility. Structural and decorrelation rate ($\hat{\rho}$) images at four time-points are shown in FIG. 4(*b*) along with the DFS ROI.

In FIG. 4(*c*), we plot transverse profiles of $\hat{\rho}$ for the DFS and DBS signals by averaging $\hat{\rho}$ across the ROI depth for the former, and by averaging $\hat{\rho}$ over three depth lines at the indicated location for the latter. As was observed in the flow phantom, the transverse decorrelation profiles from DFS are more parabolic than those associated with DBS. While there is less noise on the DFS profiles, this could be a consequence of more extensive averaging (13 depth points in the DFS ROI versus three for the DBS). The average value of $\hat{\rho}$ across the full ROI is plotted as a function of time in FIG. 4(*d*) and reveals the expected pulsatility. As a confirmation, the ratio of maximum to minimum $\hat{\rho}$ across the cardiac cycle was 2.7, consistent with prior reports.

Figure 5:
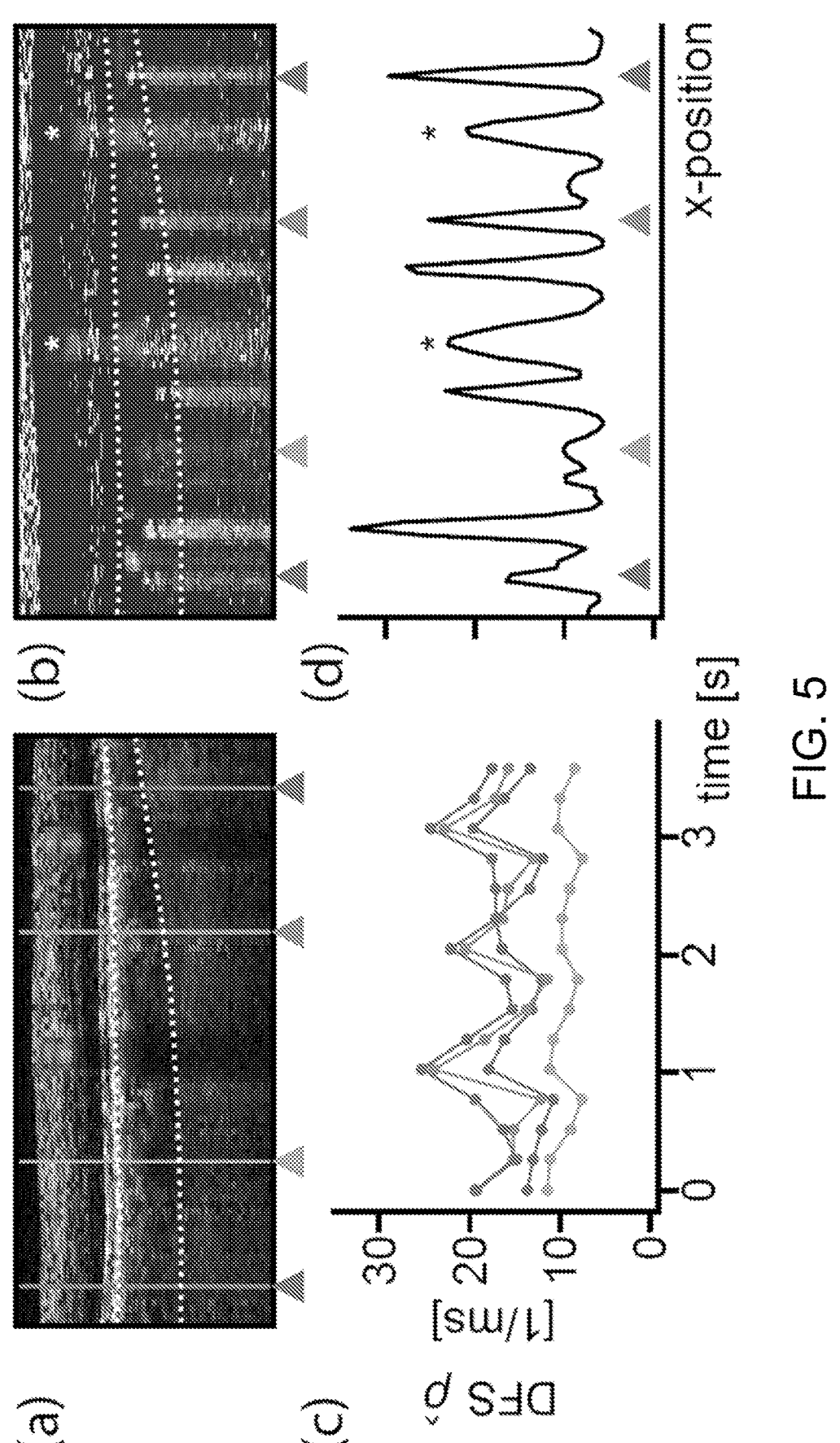
FIG. 5, panel (a) shows a cross-sectional structural image of the imaged line indicated in FIG. 4, panel (a) (the magenta line in the lower portion of the image) with RPE and chorioscleral boundaries indicated by dotted lines. Panel (b) shows the decorrelation rate $(\hat{\rho})$ image (using a rainbow color scale as in FIG. 1), where four choroidal vessel locations are selected and marked by colored triangles as in Panel (a). Panel (c) shows flow dynamics at the selected vessels and calculated by depth averaging $\hat{\rho}$ over the sclera. Panel (d) shows the decorrelation rate profile calculated by depth (over sclera) and time averaging $\hat{\rho}$. The asterisks (*) denote lateral regions wherein there is signal decorrelation due to large retinal blood vessels.

Next we applied this technique to the choroid. A combination of factors including complex and dense vascular architecture, degradation in signal quality due to the highly scattering RPE, and a low SNR make blood flow quantification in the choroid extremely challenging. We imaged a 3 mm line using an expanded M-mode B-scan protocol with 256 A-lines per location and 100 locations (30 μm spacing) (FIG. 5(*a*)). For the choroidal vessels, we analyzed DFS signals within the sclera. The boundary between the choroid and sclera is indicated in FIG. 5(*a*). FIG. 5(*b*) presents the decorrelation rates over the full image, and shows clear signals below presumed choroidal vessels. We selected four locations that align to presumed choroidal vessels (indicated by colored triangles below the images in FIGS. 5(*a*) and 5(*b*)) and plotted the average of $\hat{\rho}$ across the sclera as a function of time (FIG. 5(*c*)). Despite the limited temporal resolution of these measurements ($\approx$0.25 sec), we observed cardiac pulsatility in these vessels. The time-averaged flow profile over the 3 mm scan length, calculated by averaging $\hat{\rho}$ over the depth of the sclera and over time, is shown in FIG. 5(*d*). While these data are preliminary, they suggest promise for providing a means to quantify flow in the choroidal vasculature, a challenge for which existing solutions are quite limited.

This work discloses that the DFS signal, which is known as the source of reported "shadows" or "tails" that appear below vessels in OCT angiography, should be considered a source of reliable flow information, especially for vessels with Doppler angles close to 90°. While insensitivity to the Doppler angle was the initial motivation for this work, there are a few additional advantages of the DFS approach that merit discussion. First, we can see clearly in FIG. 2(*a*) that the DBS signal is affected by multiple-scattering as has been described by others. Although we referred to these signals as DBS, they would be more accurately labeled DBS+DFS. In analyzing them, one must contend with a signal that is modulated by a mixture of two processes. By contrast, the signal measured below a vessel (from a static scatterer) is a pure DFS signal and may, as a result, be easier to model and interpret. Second, in some applications, the DFS approach may have the advantage of providing more independent measurements of the signal dynamics than are available from the DBS approach. Consider for example the limited set of DBS voxels located inside a choroidal vessel relative to the larger set of DFS voxels in the sclera below the choroidal vessel. Third, our data suggest that the DFS signal decorrelates at approximately twice the rate of DBS signals from the center of the lumen. This could be used to accelerate flow imaging by allowing a shorter duration time-series measurement. Finally, we note that the DFS approach can be deployed simultaneously with a DBS approach; the difference is in the signal analysis. The approach can therefore be viewed as an adjunct to existing methods that can be primary for vessels that are nearly or substantially orthogonal to the direction of the interferometric light source, and secondary otherwise.

A limitation of the DFS approach is that it does not measure the depth-resolved flow within a vessel. Each DFS voxel provides a single metric that reports on the accumulated flow above the voxel. This can lead to ambiguity when multiple vessels transect the path of the beam. The degree to which this limits the utility of the approach is likely to be application dependent. In the choroid, for example, it will be difficult to always unambiguously associate the DFS properties of the sclera to a single choroidal vessel. However, this limitation should be viewed in the context of our current lack of viable approaches for flow quantification in the choroid. Because the retinal vasculature is relatively sparse, it may not be as difficult to map DFS signals in the RPE to its associated vessel. A further limitation of the DFS approach is that it might not be applicable to capillaries due to a limited DFS signal. Follow-up studies are needed to explore the range of vessel diameters for which DFS can be used.

We also note a few limitations in the methods used in this work. Doppler angles were modified by imaging the tube at different locations, which could have induced secondary changes (beam resolution/aberration) that confound the measurements. This might, for example, have caused the small linear dependence of $\hat{\rho}$ on the Doppler angle that was observed in FIG. 2(d). A single tube diameter was used in the flow phantom studies, and this diameter was toward the higher end of the relevant range for retinal and choroidal vessels. We expect that the angular dependence of DBS signals will be more severe for smaller vessels due to higher flow gradients, but this and the impact of vessel diameter on DFS signals should be further studied. Finally, as previously noted, this work operated with an assumed statistical model for DFS signals. In various embodiments, other models may be developed by experimental, numerical, or analytic methods and applied to the data collected using the disclosed procedures.

Figure 8:
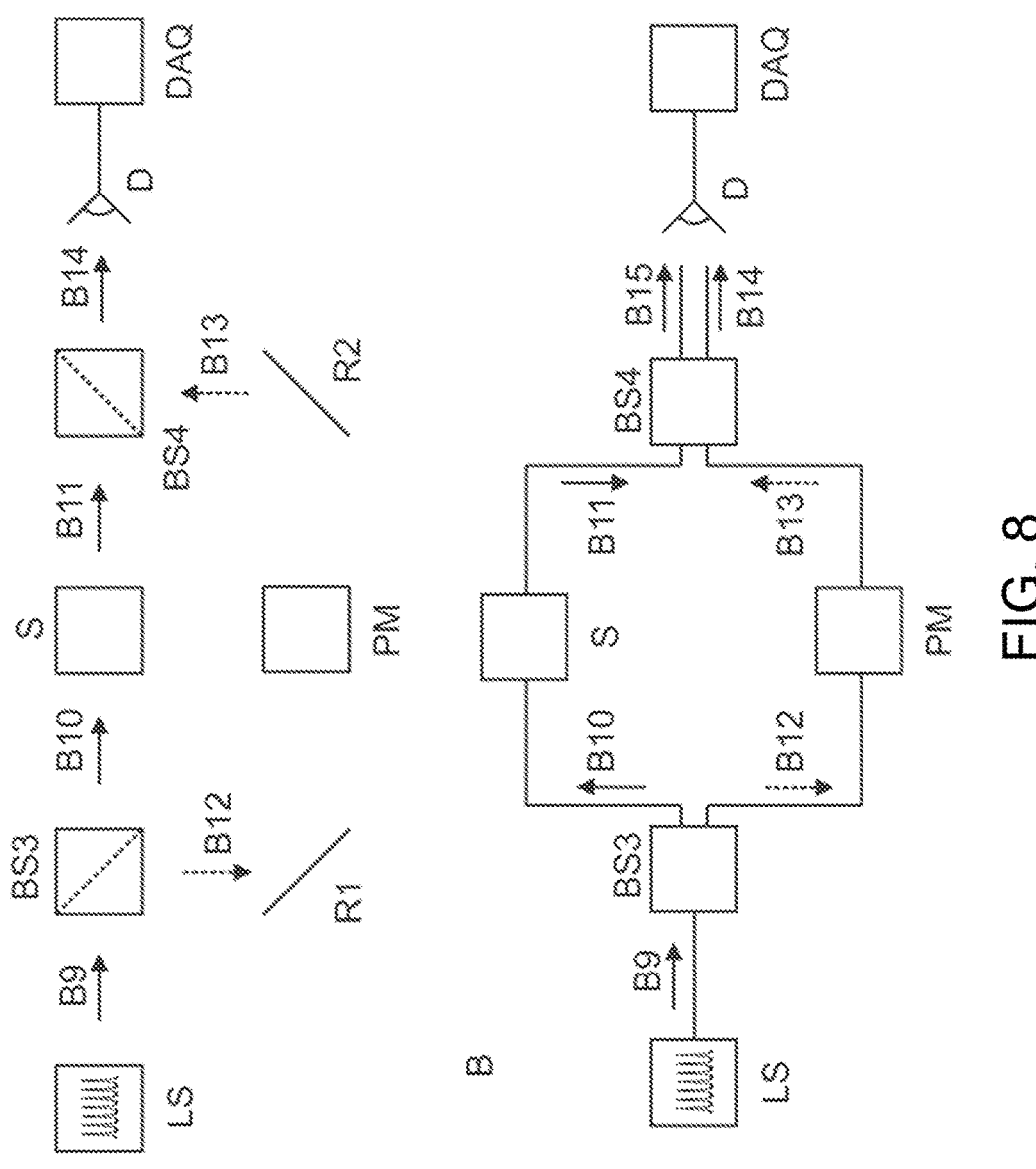
FIG. 8 provides diagrams of interferometry systems that may be used in conjunction with various embodiments disclosed herein, where panel (A) shows a Mach-Zehnder type interferometer that may be implemented using free space optics and panel (B) shows a fiber arrangement.

FIG. 8 provides diagrams of interferometry systems that may be used in conjunction with various embodiments of the invention. FIG. 8 illustrates a Mach-Zehnder type interferometer that may be implemented using free space optics (FIG. 8A) or a fiber arrangement (FIG. 8B). Other interferometer types (e.g. Michelson) can also be applied. The light source LS in either of FIG. 8A or 8B may be a wavelength-swept laser source, a wavelength-swept light source, a time-stepped optical frequency comb source, or a time-stepped discrete optical frequency source. Beam B9, emitted from LS, is directed to the interferometer input where it is split into two paths of approximately equal length using a beam splitter (BS3). B10 is directed towards a sample S (e.g. a retina in an eye of a subject). Light from the object of interest is then directed towards the interferometer output (B11). In the reference arm, beam B12 is optionally directed towards a phase modulator (PM), which can be a electro-optic phase modulator or an acousto-optic frequency shifter. The beam after the PM (i.e. beam B13) is directed to the interferometer output to interfere with beam B11 after being combined by BS4. The output beam B14 is then detected by a detector D (e.g. a photodiode). Alternatively, a fiber-based interferometer shown in FIG. 8B readily allows balanced detection due to a phase shift of IT between output beams B14 and B15. The detected signal is digitized using data collection and processing system (which may include a data acquisition board or real time oscilloscope (DAQ)) at a sampling rate $f_S$. Several wavelength sweeps (A1, A2, . . . , An) may be acquired to form a 2-dimensional or 3-dimensional image. In various embodiments, the sample arm S of the interferometer may be integrated with a patient/subject interface (e.g. lenses or a probe) which facilitates directly light into and receiving light back from a tissue of the patient or subject, e.g. from the retina. Wavelength resolved measurements provided by this interferometric system can be processed to generate depth-resolved measurements of sample reflectivity using a discrete Fourier transform within a computer system.

Alternative interferometry systems that may be used in conjunction with various embodiments of the invention may be based on the Mach-Zehnder system of FIG. 8 but replace the detector and DAQ system with a spectrometer. The spectrometer can include an optical grating and a line-scan camera. The source LS can be a broadband optical source such as a superluminescent diode, an LED source, a super-continuum source, or another light source providing broad-band optical output. Wavelength resolved measurements provided by this interferometric system can be processed to generate depth-resolved measurements of sample reflectivity using a discrete Fourier transform within a computer system.

A further interferometry system that may be used in conjunction with the various embodiments of the invention is based on the Mach-Zehnder system of FIG. 8 but in which the source LS can be a broadband optical source such as a superluminescent diode, an LED source, a supercontinuum source, or another light source providing broadband optical output. The detector and DAQ measure a low-coherence interferometry fringe to measure the reflectivity at a single depth point following known time-domain OCT methods. The reference path B12 can include a variable optical delay to scan the location of this depth-resolved measurement. The phase modulator PM can be used to generate encode the inference signal with a specific carrier frequency that is determined by the signal provided to the phase modulator. Alternatively, the phase modulator can be an acousto-optic frequency shift provided with a RF signal at frequency Fao and causes the interference signal to be located at the RF frequency Fao.

The Mach-Zehnder interferometer arrangement presented in FIG. 8 and used in further interferometer system embodiments can be replaced with alternative architectures that provide light in at least a sample path and a reference path. These include Michelson interferometer systems and Mach-Zehnder systems in which at least one of the sample or reference path includes a portion that is bidirectional.

Computer and Optical Systems

Figure 9:
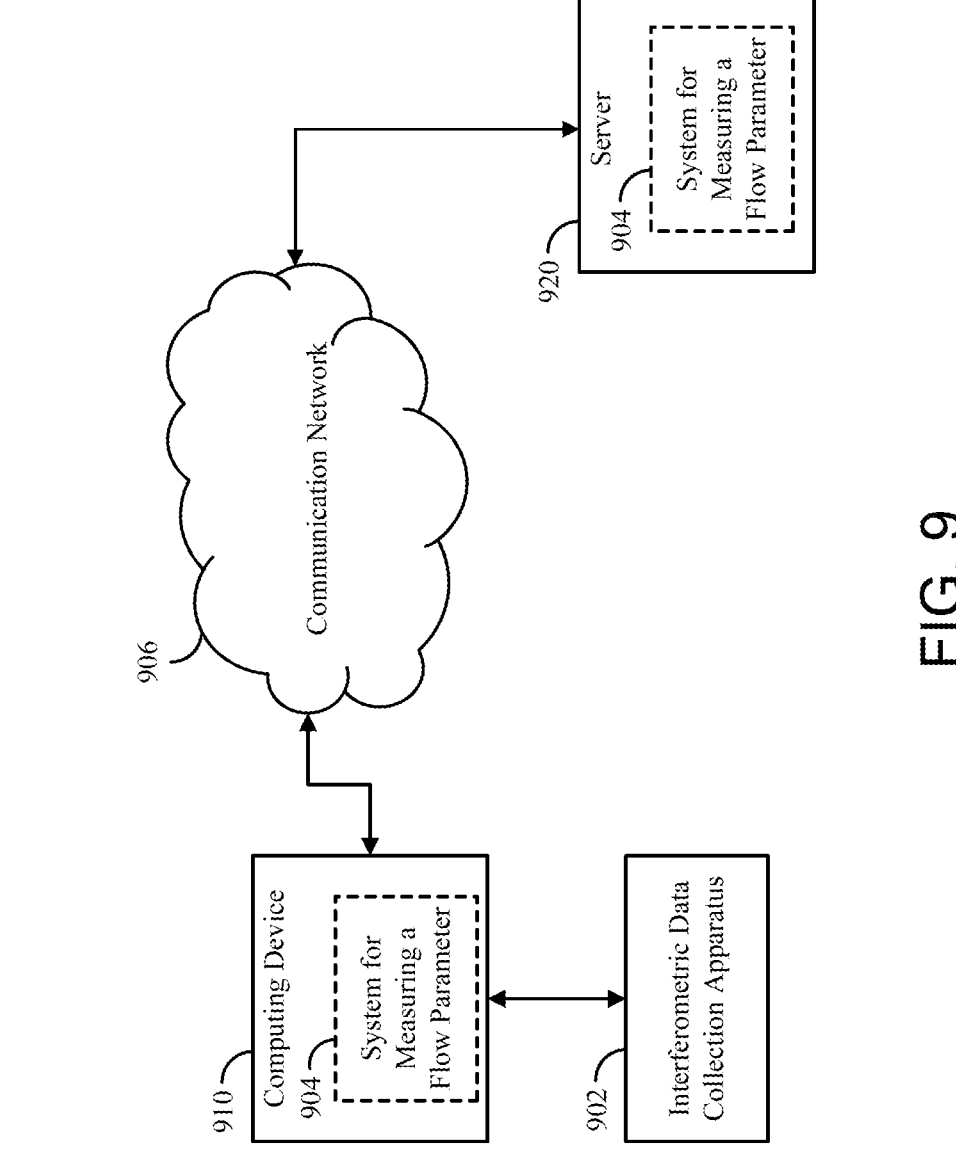
FIG. 9 shows an example of a system for measuring a flow parameter in accordance with some embodiments of the disclosed subject matter.

Turning to FIG. 9, an example 900 of a system (e.g. a data collection and processing system) for measuring a flow parameter is shown in accordance with some embodiments of the disclosed subject matter. In some embodiments, a computing device 910 can execute at least a portion of a system for measuring a flow parameter 904 and provide control signals to an interferometric data collection apparatus 902. Additionally or alternatively, in some embodiments, computing device 910 can communicate information regarding the control signals to or from a server 920 over a communication network 906, which can execute at least a portion of system for measuring a flow parameter 904. In some such embodiments, server 920 can return information to computing device 910 (and/or any other suitable computing device) relating to the control signals for system for measuring a flow parameter 904. This information may be transmitted and/or presented to a user (e.g. a researcher, an operator, a clinician, etc.) and/or may be stored (e.g. as part of a research database or a medical record associated with a subject).

In some embodiments, computing device 910 and/or server 920 can be any suitable computing device or combination of devices, such as a desktop computer, a laptop computer, a smartphone, a tablet computer, a wearable computer, a server computer, a virtual machine being executed by a physical computing device, etc. As described herein, system for measuring a flow parameter 904 can present information about the control signals to a user (e.g., researcher and/or physician).

In some embodiments, communication network 906 can be any suitable communication network or combination of communication networks. For example, communication network 906 can include a Wi-Fi network (which can include one or more wireless routers, one or more switches, etc.), a peer-to-peer network (e.g., a Bluetooth network), a cellular network (e.g., a 4G network, a 5G network, etc., complying with any suitable standard, such as CDMA, GSM, LTE, LTE Advanced, WiMAX, etc.), a wired network, etc. In some embodiments, communication network 906 can be a local area network, a wide area network, a public network (e.g., the Internet), a private or semi-private network (e.g., a corporate or university intranet), any other suitable type of network, or any suitable combination of networks. Communications links shown in FIG. 9 can each be any suitable communications link or combination of communications links, such as wired links, fiber optic links, Wi-Fi links, Bluetooth links, cellular links, etc.

Figure 10:
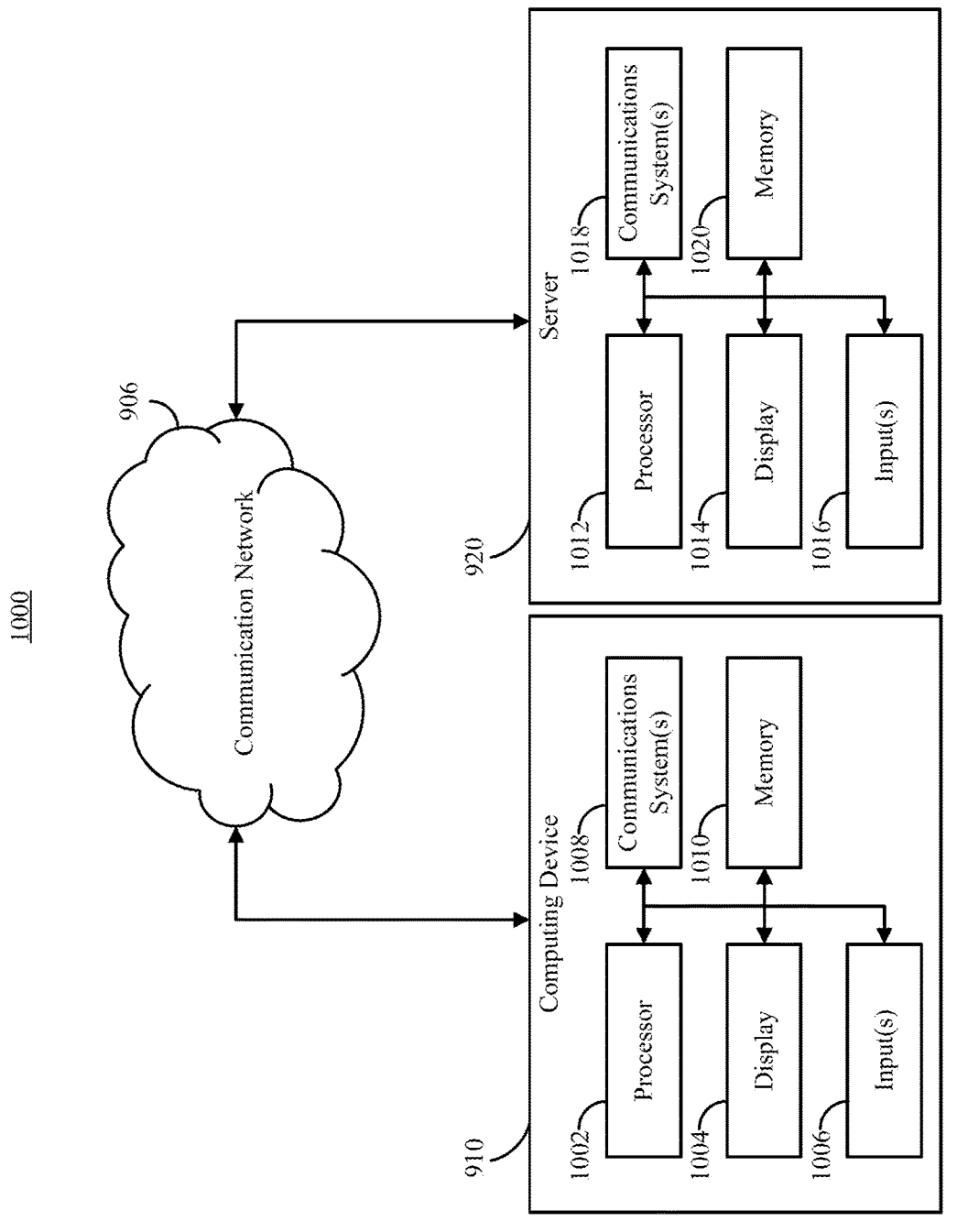
FIG. 10 shows an example of hardware that can be used to implement a computing device and server in accordance with some embodiments of the disclosed subject matter.

FIG. 10 shows an example 1000 of hardware that can be used to implement computing device 910 and server 920 in accordance with some embodiments of the disclosed subject matter. As shown in FIG. 10, in some embodiments, computing device 910 can include a processor 1002, a display 1004, one or more inputs 1006, one or more communication systems 1008, and/or memory 1010. In some embodiments, processor 1002 can be any suitable hardware processor or combination of processors, such as a central processing unit, a graphics processing unit, etc. In some embodiments, display 1004 can include any suitable display devices, such as a computer monitor, a touchscreen, a television, etc. In some embodiments, inputs 1006 can include any suitable input devices and/or sensors that can be used to receive user input, such as a keyboard, a mouse, a touchscreen, a microphone, etc.

In some embodiments, communications systems 1008 can include any suitable hardware, firmware, and/or software for communicating information over communication network 906 and/or any other suitable communication networks. For example, communications systems 1008 can include one or more transceivers, one or more communication chips and/or chip sets, etc. In a more particular example, communications systems 1008 can include hardware, firmware and/or software that can be used to establish a Wi-Fi connection, a Bluetooth connection, a cellular connection, an Ethernet connection, etc.

In some embodiments, memory 1010 can include any suitable storage device or devices that can be used to store instructions, values, etc., that can be used, for example, by processor 1002 to present content using display 1004, to communicate with server 920 via communications system(s) 1008, etc. Memory 1010 can include any suitable volatile memory, non-volatile memory, storage, or any suitable combination thereof. For example, memory 1010 can include RAM, ROM, EEPROM, one or more flash drives, one or more hard disks, one or more solid state drives, one or more optical drives, etc. In some embodiments, memory 1010 can have encoded thereon a computer program for controlling operation of computing device 910. In such embodiments, processor 1002 can execute at least a portion of the computer program to present content (e.g., images, user interfaces, graphics, tables, etc.), receive content from server 920, transmit information to server 920, etc.

In some embodiments, server 920 can include a processor 1012, a display 1014, one or more inputs 1016, one or more communications systems 1018, and/or memory 1020. In some embodiments, processor 1012 can be any suitable hardware processor or combination of processors, such as a central processing unit, a graphics processing unit, etc. In some embodiments, display 1014 can include any suitable display devices, such as a computer monitor, a touchscreen, a television, etc. In some embodiments, inputs 1016 can include any suitable input devices and/or sensors that can be used to receive user input, such as a keyboard, a mouse, a touchscreen, a microphone, etc.

In some embodiments, communications systems 1018 can include any suitable hardware, firmware, and/or software for communicating information over communication network 906 and/or any other suitable communication networks. For example, communications systems 1018 can include one or more transceivers, one or more communication chips and/or chip sets, etc. In a more particular example, communications systems 1018 can include hardware, firmware and/or software that can be used to establish a Wi-Fi connection, a Bluetooth connection, a cellular connection, an Ethernet connection, etc.

In some embodiments, memory 1020 can include any suitable storage device or devices that can be used to store instructions, values, etc., that can be used, for example, by processor 1012 to present content using display 1014, to communicate with one or more computing devices 910, etc. Memory 1020 can include any suitable volatile memory, non-volatile memory, storage, or any suitable combination thereof. For example, memory 1020 can include RAM, ROM, EEPROM, one or more flash drives, one or more hard disks, one or more solid state drives, one or more optical drives, etc. In some embodiments, memory 1020 can have encoded thereon a server program for controlling operation of server 920. In such embodiments, processor 1012 can execute at least a portion of the server program to transmit information and/or content (e.g., results of a tissue identification and/or classification, a user interface, etc.) to one or more computing devices 910, receive information and/or content from one or more computing devices 910, receive instructions from one or more devices (e.g., a personal computer, a laptop computer, a tablet computer, a smartphone, etc.), etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

FIG. 11 shows an example 1100 of a process for measuring a blood flow parameter in a blood vessel in accordance with some embodiments of the disclosed subject matter. As shown in FIG. 11, at 1102, process 1100 can provide an interferometric data collection apparatus including a light source and a sensor coupled to a controller. At 1104, process 1100 can direct, using the controller, the light source toward a proximal side of a blood vessel. At 1106, process 1100 can obtain, using the controller, interferometric data from a tissue adjacent to and outside of a distal side of the blood vessel opposite the proximal side. At 1108, process 1100 can determine, using the controller, a signal modulation rate based on the interferometric data. Finally, at 1110, process 1100 can estimate, using the controller, a blood flow parameter in the blood vessel based on the signal modulation rate.

It should be understood that the above described steps of the process of FIG. 11 can be executed or performed in any order or sequence not limited to the order and sequence shown and described in the figures. Also, some of the above steps of the processes of FIG. 11 can be executed or performed substantially simultaneously where appropriate or in parallel to reduce latency and processing times.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

What is claimed is:

1. An apparatus for measuring a flow parameter in a vessel, comprising:
an interferometric data collection apparatus comprising a light source and a sensor coupled to a controller, the controller being configured to:
direct the light source toward a proximal side of a vessel;
obtain interferometric data from a sample adjacent to and outside of a distal side of the vessel opposite the proximal side;
determine a signal modulation rate based on the interferometric data; and
estimate a flow parameter in the vessel based on the signal modulation rate.

2. The apparatus of claim 1, wherein the signal modulation rate comprises a decorrelation rate.

3. The apparatus of claim 1, wherein the light source is directed in an orientation that is substantially orthogonal to a central axis of the vessel.

4. The apparatus of claim 1, wherein the interferometric data collection apparatus comprises an optical coherence tomography (OCT) apparatus, and
wherein the controller, when obtaining interferometric data, is further configured to:
obtain OCT data from the sample adjacent to and outside of the distal side of the vessel opposite the proximal side, and
wherein the controller, when determining a signal modulation rate based on the interferometric data, is further configured to:
determine the signal modulation rate based on the OCT data.

5. The apparatus of claim 4, wherein the OCT data is based on forward-scattering of light from the light source by material flowing in the vessel into the sample adjacent to and outside of the distal side of the vessel.

6. The apparatus of claim 5, wherein the controller, when estimating a flow parameter in the vessel, is further configured to:
estimate the flow parameter in the vessel, wherein the flow parameter is based on accumulated flow throughout the vessel.

7. The apparatus of claim 1, wherein the vessel and the sample are located in a biological tissue in vitro, a biological tissue ex vivo, a designed phantom including fluidic channels, a flow phantom or a microfluidic platform.

8. The apparatus of claim 1, wherein the flow parameters include at least one of flow speed, velocity, or flux.

9. The apparatus of claim 1, wherein the controller, when obtaining interferometric data from a sample adjacent to and outside of a distal side of the vessel opposite the proximal side, is further configured to:
obtain back-scattered interferometric data from inside the vessel, wherein the controller, when determining a signal modulation rate based on the interferometric data, is further configured to:
determine a back-scattered signal modulation rate based on the back-scattered interferometric data, and
wherein the controller, when estimating a flow parameter in the vessel based on the signal modulation rate, is further configured to:
estimate the flow parameter in the vessel based on the back-scattered signal modulation rate.

10. The apparatus of claim 1, wherein the vessel comprises a blood vessel, and
wherein the sample comprises a tissue.

11. The apparatus of claim 10, wherein the blood vessel and the tissue are located in a retina of a subject.

12. The apparatus of claim 11, wherein the tissue comprises at least one of scleral tissue or retinal pigment epithelium (RPE) tissue adjacent to and outside of the distal side of the blood vessel.

13. A method for measuring a flow parameter in a vessel, comprising:
providing an interferometric data collection apparatus comprising a light source and a sensor coupled to a controller;
directing, using the controller, the light source toward a proximal side of a vessel;
obtaining, using the controller, interferometric data from a sample adjacent to and outside of a distal side of the vessel opposite the proximal side;
determining, using the controller, a signal modulation rate based on the interferometric data; and
estimating, using the controller, a flow parameter in the vessel based on the signal modulation rate.

14. The method of claim 13, wherein determining a signal modulation rate further comprises:
determining a decorrelation rate based on the interferometric data, and wherein estimating a flow parameter in the vessel further comprises:
estimating the flow parameter in the vessel based on the decorrelation rate.

15. The method of claim 13, wherein directing the light source toward a proximal side of a vessel further comprises:
directing the light source toward a proximal side of the vessel in an orientation that is substantially orthogonal to a central axis of the vessel.

16. The method of claim 13, wherein the interferometric data collection apparatus comprises an optical coherence tomography (OCT) apparatus, and
wherein obtaining interferometric data further comprises:
obtaining OCT data from the sample adjacent to and outside of the distal side of the vessel opposite the proximal side, and
wherein determining a signal modulation rate based on the interferometric data further comprises:
determining the signal modulation rate based on the OCT data.

17. The method of claim 16, wherein the OCT data is based on forward-scattering of light from the light source by material flowing in the vessel into the sample adjacent to and outside of the distal side of the vessel.

18. The method of claim 17, wherein estimating a flow parameter in the vessel further comprises:
estimating the flow parameter in the vessel, wherein the flow parameter is based on accumulated flow throughout the vessel.

19. The method of claim 13, wherein the vessel and the sample are located in a biological tissue in vitro, a biological tissue ex vivo, a designed phantom including fluidic channels, a flow phantom or a microfluidic platform.

20. The method of claim 13, wherein the flow parameters include at least one of flow speed, velocity, or flux.

21. The method of claim 13, wherein obtaining interferometric data from a sample adjacent to and outside of a distal side of the vessel opposite the proximal side further comprises:

obtaining back-scattered interferometric data from inside the vessel, wherein determining a signal modulation rate based on the interferometric data further comprises:

determining a back-scattered signal modulation rate based on the back-scattered interferometric data, and wherein estimating a flow parameter in the vessel based on the signal modulation rate further comprises:

estimating the flow parameter in the vessel based on the back-scattered signal modulation rate.

22. The method of claim 13, wherein the vessel comprises a blood vessel, and wherein the sample comprises a tissue.

23. The method of claim 22, wherein the blood vessel and the tissue are located in a retina of a subject.

24. The method of claim 23, wherein the tissue comprises at least one of scleral tissue or retinal pigment epithelium (RPE) tissue adjacent to and outside of the distal side of the blood vessel.

* * * * *